United States Patent [19]

Nishida et al.

[11] 4,378,348

[45] Mar. 29, 1983

[54] OA-7653 SUBSTANCE

[75] Inventors: Tsutomu Nishida; Michiharu Sugawara; Takashi Kamogashira, all of Tokushima, Japan

[73] Assignee: Otsuka Pharmaceutical Co., Ltd., Japan

[21] Appl. No.: 197,103

[22] PCT Filed: Mar. 8, 1980

[86] PCT No.: PCT/JP80/00041

§ 371 Date: Sep. 16, 1980

§ 102(e) Date: Sep. 16, 1980

[30] Foreign Application Priority Data

Dec. 28, 1979 [JP] Japan ................................ 54-173808
May 23, 1980 [JP] Japan ................................ 55-69218

[51] Int. Cl.$^3$ ............................................. A61K 35/00
[52] U.S. Cl. .................................................... 424/118
[58] Field of Search ......................................... 424/118

[56]     References Cited

PUBLICATIONS

McCormick et al., Antibiotics Annual, 1955–1956, 1956, pp. 606–611.

*Primary Examiner*—Jerome D. Goldberg
*Attorney, Agent, or Firm*—Larson and Taylor

[57]     ABSTRACT

The antibiotic of the invention is produced from a novel strain belonging to *Streptomyces hygroscopicus*, acts against various bacteria and is useful, for example, as active components of antibacterial compositions.

2 Claims, 13 Drawing Figures

OA-7653 SUBSTANCE

TECHNICAL FIELD

This invention relates to a novel antibiotic prepared from a novel strain belonging to *Streptomyces hygroscopicus* and to antibacterial compositions comprising the antibiotic.

BACKGROUND ART

While we have found that the strain of this invention belongs to *Streptomyces hygroscopicus* as will be described later, the strain is clearly distinct from *Streptomyces hygroscopicus* (Jensen) and *Streptomyces hygroscopicus* ISP 5578 which are typical of the species and is also distinct from the strains belonging to any known species or subspecies. Further the substance of this invention can not be isolated from the strains of any of known species or subspecies.

DISCLOSURE OF INVENTION

The substance of the invention is characterized by the following physicochemical properties.

(1) Appearance

White particulate crystals.

(2) Solubility

Sparingly soluble in 0.1 N aqueous solution of hydrochloric acid.

Insoluble in methanol, ethanol, butanol, acetone and ethyl acetate.

Soluble in 0.1 N aqueous solution of sodium hydroxide.

(3) Specific rotatory power $[\alpha]_D^{23.5} = +76.5°$ (C=0.463, water)

(4) Elementary analysis

C: 46.10%, H: 4.47%, N: 7.18%.

(5) Molecular weight determined by ultra-centrifugal analysis About 2000

(6) Isoelectric point determined by electrophoresis pH 5–6

Figure 3:
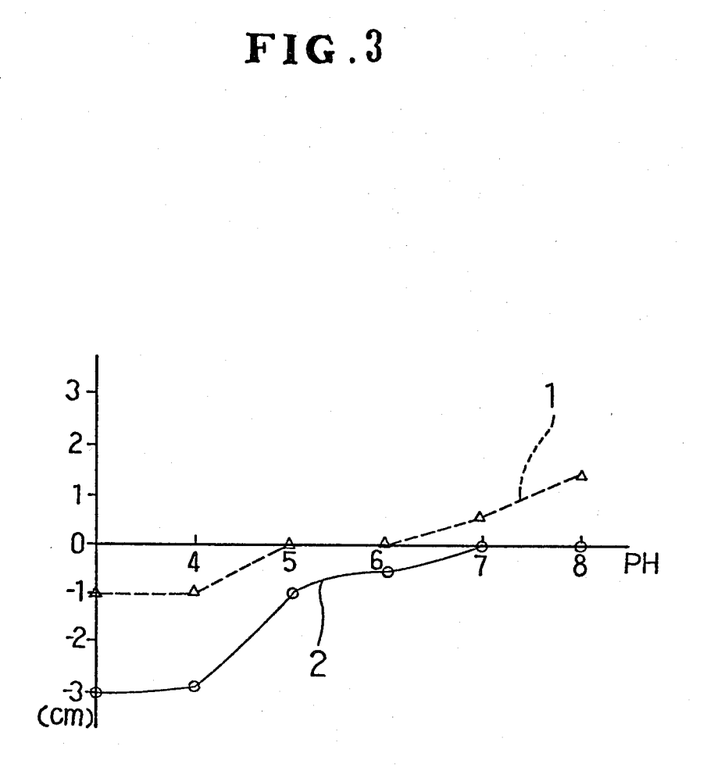
FIG. 3 is a diagram showing the results of electrophoretic analysis of OA-7653 substance of the invention and vancomycin serving as a control substance.

The isoelectric point is determined by the following method. In 1 liter of distilled water are dissolved 6.008 g of citric acid, 3.893 g of $KH_2PO_4$, 1.769 g of $H_3PO_4$ and 5.266 g of 5,5-diethylbarbituric acid. One-liter quantities of such solution are adjusted to pH 3, 4, 5, 6, 7 and 8 with 0.2 N aqueous sodium hydroxide solution to obtain buffer solutions. Using the buffer solutions and Whatman filter paper No. 1 (product of W. and R. Balston Ltd.) spotted with an aqueous solution of the substance of the invention, the substance is subjected to electrophoresis at 300 V for 4 hours to obtain an analysis diagram. The result is represented by Curve 1, FIG. 3, which shows that the isoelectric point is at pH 5 to 6.

(7) IR absorption spectrum

Figure 4:
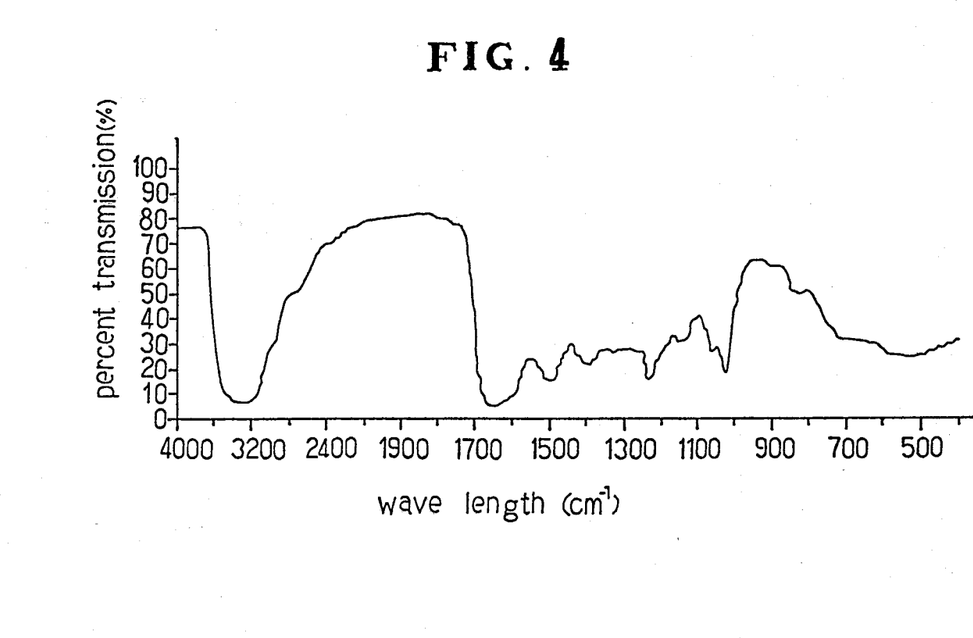
FIG. 4 is a diagram showing an IR spectrum of the present substance.

FIG. 4 shows an IR absorption spectrum obtained with use of a KBr disk, indicating main absorption peaks at 3280 (s), 1660 (s), 1640 (s), 1515 (s), 1490 (s), 1395 (s), 1235 (s), 1150 (m), 1062 (s) and 1020 (s) $cm^{-1}$.

Figure 5:
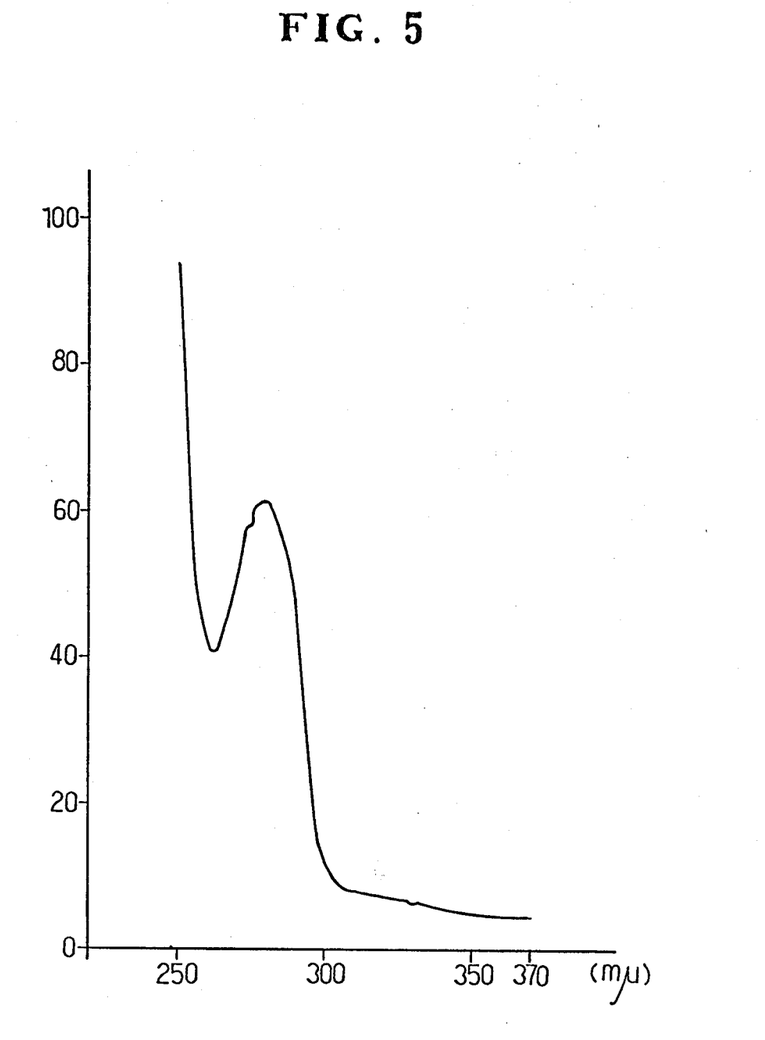
FIGS. 5 to 7 are diagrams showing UV absorption spectra of the present substance.

(8) UV absorption spectra (i) The substance of the invention (1 mg/10 ml) is subjected to UV analysis at a cell length of 1 cm, using 0.1 N aqueous solution of hydrochloric acid as a solvent. FIG. 5 showing the result reveals an absorption maximum at 278 m$\mu$ ($E_{1\%}^{1\ cm} = 56$).

Figure 6:
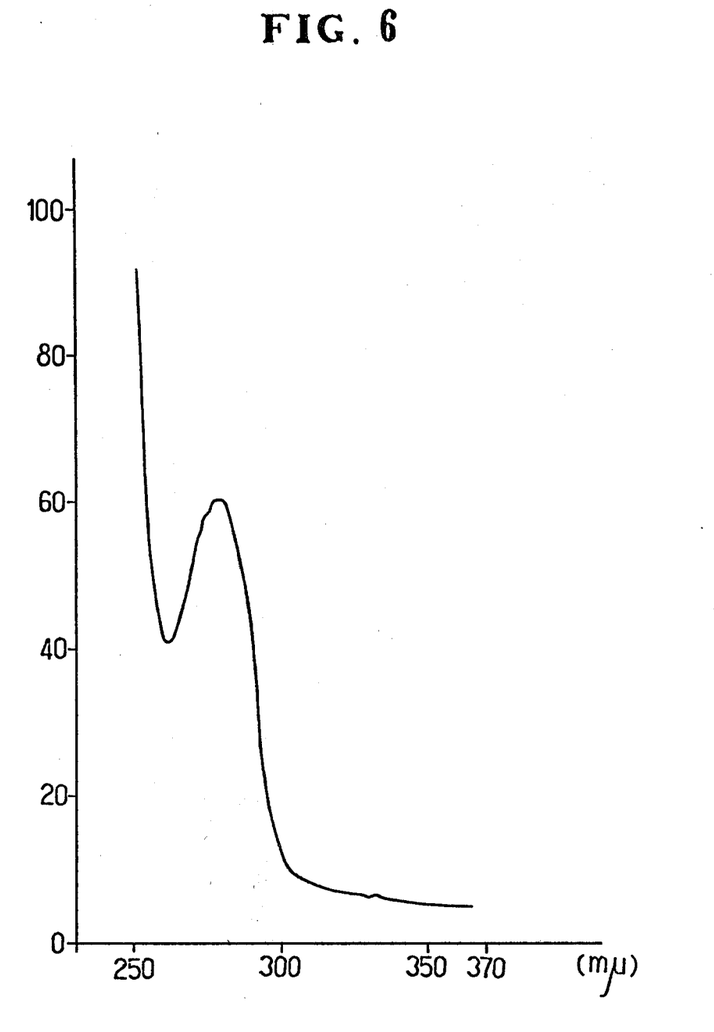

(ii) FIG. 6 shows the result of UV analysis similarly conducted with use of distilled water as a solvent. The spectrum reveals an absorption maximum also at 278 m$\mu$ ($E_{1\%}^{1\ cm} = 56$).

Figure 7:
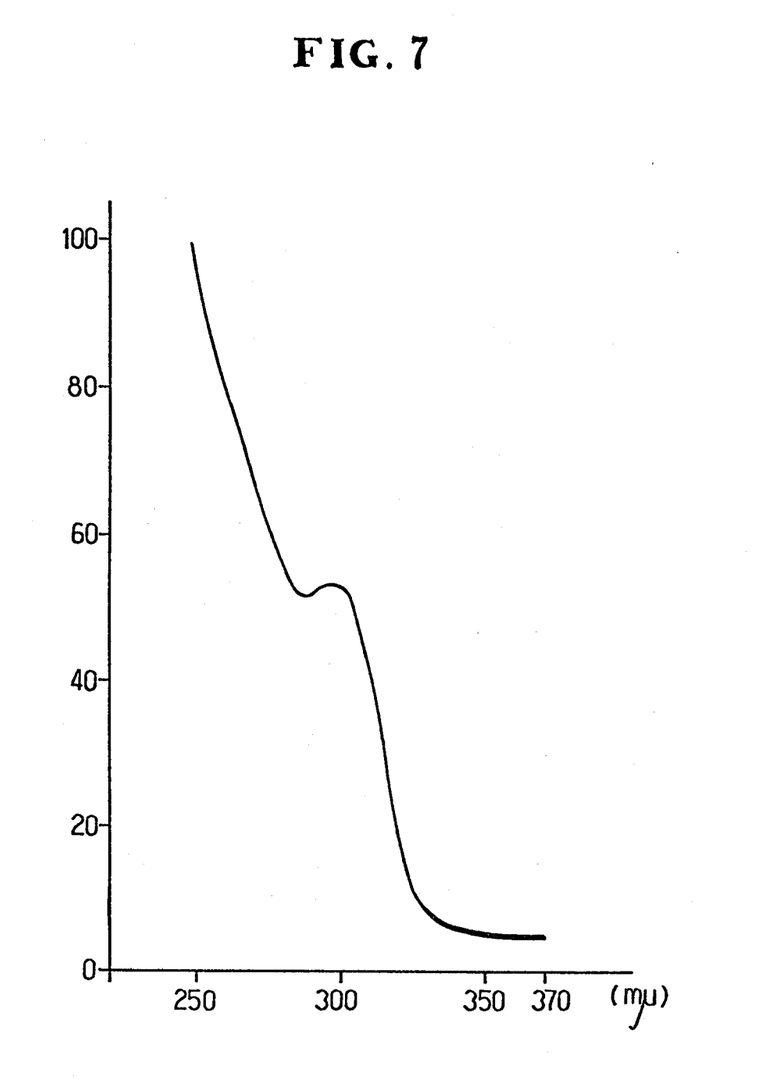

(iii) The substance of the invention (0.5 mg/10 ml) is subjected to UV analysis at a cell length of 1 cm, using 0.1 N aqueous solution of sodium hydroxide as a solvent. FIG. 7 showing the result reveals an absorption maximum at 298 m$\mu$ ($E_{1\%}^{1\ cm} = 100.8$).

(9) $^1$H-NMR spectrum

Figure 8:
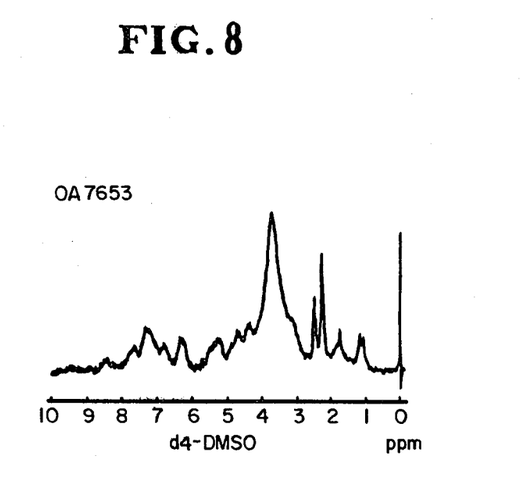
FIGS. 8 and 9 are diagrams showing $^1$H-NMR spectra of the present substance and vancomycin.

FIG. 8 shows a $^1$H-HMR spectrum of the present substance in dimethyl sulfoxide substituted with deuterium ($d^6$-DMSO). Table 1 below shows the shifts (ppm) of peaks.

TABLE 1

| No. | ppm | No. | ppm | No. | ppm |
|---|---|---|---|---|---|
| 1 | 1.05–1.35 | 5 | 3.0–4.1 | 9 | 6.6–7.0 |
| 2 | 1.60–2.0 | 6 | 4.2–4.9 | 10 | 7.0–7.55 |
| 3 | 2.2 | 7 | 5.05–5.6 | 11 | 7.6–8.0 |
| 4 | 2.50 | 8 | 6.3–6.5 | | |

(10) $^{13}$C-NMR spectrum

Figure 10:
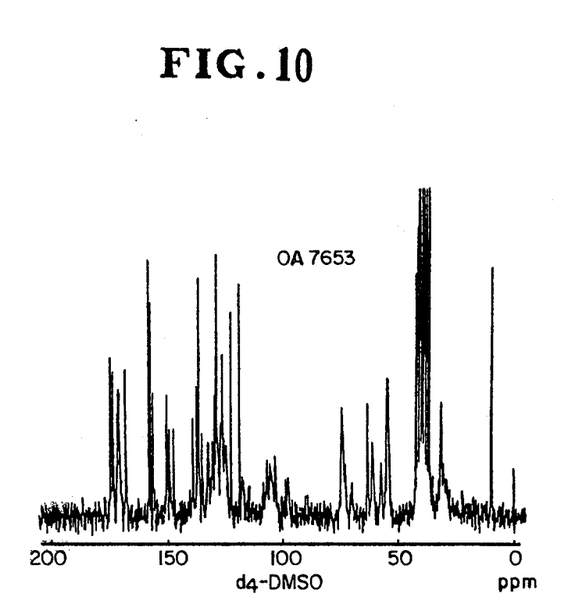
FIG. 10 is a diagram showing $^{13}$C-NMR spectrum of the present substance.

FIG. 10 shows a $^{13}$C-NMR spectrum of the present substance in $d^6$-DMSO. Table 2 below shows the shifts (ppm) of peaks.

TABLE 2

| No. | ppm | No. | ppm | No. | ppm |
|---|---|---|---|---|---|
| 1 | 173.2 | 14 | 148.7 | 27 | 105.9 |
| 2 | 173.0 | 15 | 146.8 | 28 | 104.6 |
| 3 | 172.4 | 16 | 138.3 | 29 | 102.3 |
| 4 | 172.2 | 17 | 136.5 | 30 | 96.3 |
| 5 | 170.8 | 18 | 135.5 | 31 | 73.6 |
| 6 | 169.7 | 19 | 134.1 | 32 | 69.3 |
| 7 | 169.0 | 20 | 131.6 | 33 | 62.5 |
| 8 | 167.1 | 21 | 129.7 | 34 | 60.6 |
| 9 | 157.0 | 22 | 128.8 | 35 | 56.7 |
| 10 | 156.8 | 23 | 127.8 | 36 | 53.9 |
| 11 | 155.8 | 24 | 125.3 | 37 | 31.1 |
| 12 | 149.7 | 25 | 121.5 | 38 | 9.6 |
| 13 | 149.5 | 26 | 117.9 | | |

(11) Thin-layer chromatography

The substance of the invention is dissolved in water and subjected to thin-layer chromatography with use of a thin-layer plate of "Silica Gel 60 $F_{254}$" (product of Merck), with the following results.

(i) Developing solvent: butanol-acetic acid-water (4:1:1 in volume ratio). Rf=0.
(ii) Developing solvent: propanol-2 N ammonia water (7:3 in volume ratio). Rf=0.
(iii) Developing solvent: chloroform-ethanol-water (4:7:2 in volume ratio). Rf=0.45.
(iv) Developing solvent: ethanol-water (7:3 in volume ratio). Rf=0.8.

(12) Paper chromatography

The substance of the invention is dissolved in water and subjected to paper chromatography with use of Whatman chromatographic paper, Whatman No. 1.

The results are as follows.

(i) Developing solvent: butanol-acetic acid-water (4:3:7 in volume ratio). Rf=0.83.
(ii) Developing solvent: butanol-pyridine-water (4:3:7 in volume ratio). Rf=0.76.

(13) Color reactions

The substance of the invention is dissolved in water and subjected to color reactions on the same TLC plates as used for the tin-layer chromatography above. The results are as follows.

| Iodine reaction | Positive |
|---|---|
| Ninhydrin reaction | " |
| Molisch reaction | " |
| Ehrlich's reaction | " |

Amino acid analysis and gas chromatographic analysis have revealed that the substance of this invention contains 0.58μ mole/mg of L-glutamic acid and 0.64μ mole/mg of glucose as components thereof.

The substance of the invention is further characterized by its antibacterial activity.

The activity of the substance against various bacteria is determined in terms of minimal inhibitory concentrations (MIC) according to agar-dilution tests (culture medium: Heart Infusion (product of Eiken Kagaku Co., Ltd., Japan), incubation: 37° C., 18 hours). Table 3 below shows the results thus determined.

TABLE 3

| Test No. | Test bacteria | MIC (mcg/ml) |
|---|---|---|
| 1 | Bacillus subtilis PCI-219 | 6.25 |
| 2 | Bacillus anthracis | 12.5 |
| 3 | Bacillus cereus IFO 3001 | 12.5 |
| 4 | Bacillus cereus IFO 3466 | 12.5 |
| 5 | Bacillus cereus ATCC 11778 | 12.5 |
| 6 | Bacillus pumilus IFO 3813 | 6.25 |
| 7 | Bacillus circulans ATCC 8241 | 6.25 |
| 8 | Staphylococcus aureus FDA 209P | 3.13 |
| 9 | Staphylococcus aureus Newman | 3.13 |
| 10 | Staphylococcus aureus IFO 3060 (Terazima) | 6.25 |
| 11 | Staphylococcus aureus Smith | 6.25 |
| 12 | Staphylococcus epidermidis IFO 3762 | 12.5 |
| 13 | Streptococcus pyogenes aureus | 3.13 |
| 14 | Streptococcus pyogenes IID S23 | 6.25 |
| 15 | Streptococcus faecalis IFO 12580 | 6.25 |
| 16 | Streptococcus viridans | 3.13 |
| 17 | Sarcina lutea PCI-1001 | 3.13 |
| 18 | Salmonella typhi O-901 NCTC 8393 | >100 |
| 19 | Proteus vulgaris IID OX-19 us | >100 |
| 20 | Yersinia enterocolitica O-3 | >100 |
| 21 | Candida albicans KYU | >100 |
| 22 | Saccharomyces cerevisiae | >100 |
| 23 | Mycobacterium phlei IFO 3158 | 12.5 |
| 24 | Mycobacterium smegmatis ATCC 607 | 25 |
| 25 | Mycobacterium smegmatis IFO 3083 | 1.56 |
| 26 | Mycobacterium avium IFO 3082 | 25 |

The substance of this invention was intravenously administered to male mice of DD strain weighing 20 to 21 g and checked for acute toxicity. Consequently no death resulted at a dose of 1500 mg/kg. Biopsy of all the survivals revealed no noticeable influence on organs.

Figure 9:
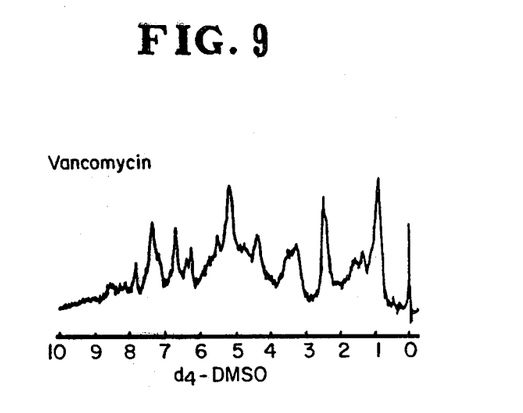
Figure 11:
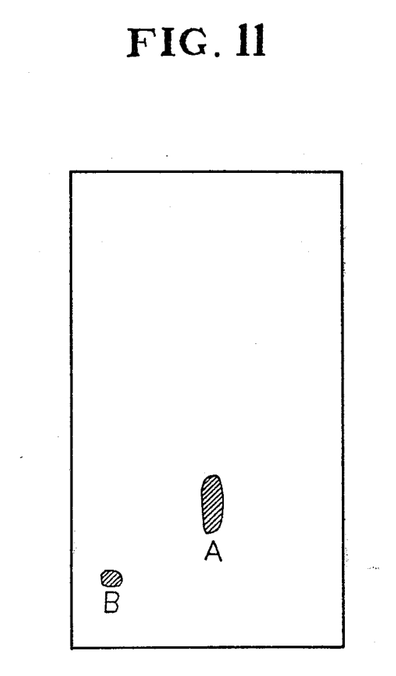
FIGS. 11 to 13 are diagrams showing the results of TLC analysis of the present substance and vancomycin hydrochloride.
Figure 12:
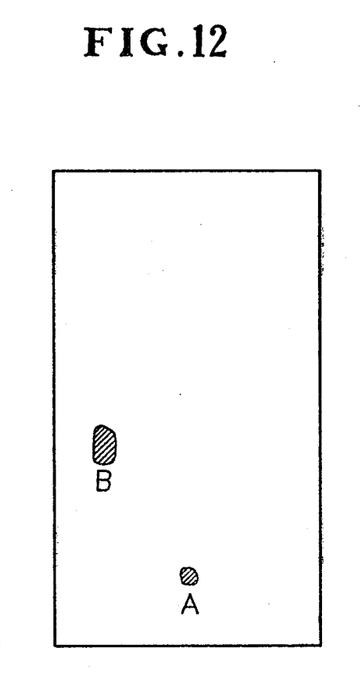
Figure 13:
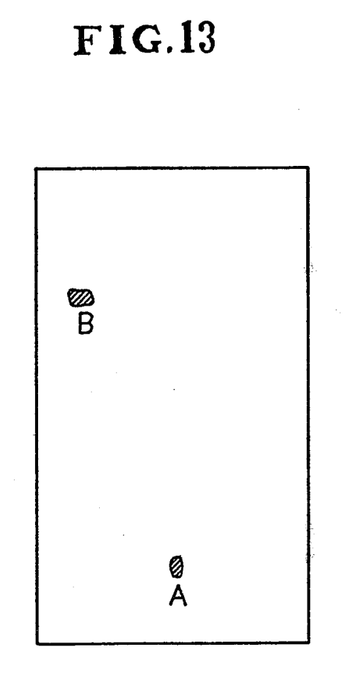

In view of the physiochemical properties and the pharmacological test results stated above, in combination with the origin of the present compound, the compound appears most analogous to vancomycin, a known antibiotic [Shionogi's Annual Report, Vol. 7, p. 465 (1957), Antibiotics Annual, 1957-1958, p. 906 (1958), Journal of Medical Chemistry, Vol. 8, p. 18 (1965), and Antibiotics Annual, 1955-1956, p. 606 (1956)]. However, vancomycin is produced from *Streptomyces orientalis* as will be described later. As disclosed in the above literature, it proves negative when subjected to ninhydrin reaction and Ehrlich's reaction. An electrophoretic analysis of the compound in the form of vancomycin hydrochloride shows that it has an isoelectric point at a pH of 7 to 8 as represented by Curve 2 in FIG. 3. FIG. 9 showing a $^1$H-NMR spectrum of vancomycin hydrochloride reveals that the spectral chart differs from that of the present invention. TLC analyses with use of the developing solvents mentioned in para. (11), (ii) to (iv) show that vancomycin hydrochloride exhibits the spots indicated at A in FIGS. 11 to 13 (in which indicated at B are the spots developed out with use of the present substance as an aqueous solution). When tested for acute toxicity by intravenous administration to male mice of DD strain weighing 20 to 21 g, vancomycin exhibits LD$_{50}$ of 400 to 500 mg/kg. In these features, vancomycin distinctly differs from the substance of the invention. Additionally vancomycin contains aspartic acid as a component thereof but contains no glutamic acid as disclosed in J. Med. Chem., Vol. 8, p. 18 (1965). In this respect also, the present substance differs from vancomycin. Although we have compared the present substance with various known antiobiotics derived from microorganisms, especially from those belonging to the genus Streptomyces like the present substance, none other than vancomycin have been found analogous to the present substance. Thus we have identified the substance of this invention, OA-7653 substance, as a novel compound.

The novel substance of the invention, namely, OA-7653 substance is produced from a strain belonging to *Streptomyces hygroscopicus*.

We have isolated the strain from soil in Hiwasa-cho, Kaifu-gun, Tokushima-ken, Japan. The strain has the following features and has been identified as a novel strain.

I. Morphology

Figure 1:
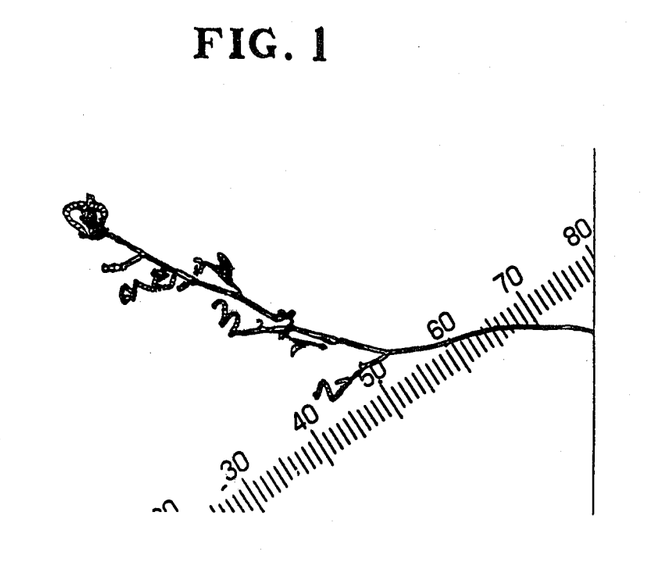
FIG. 1 is a photomicrograph and FIG. 2 is a electron-micrograph showing Streptomyces hygroscopicus subsp. hiwasaensis FB-5 useful for producing OA-7653 substance of the invention.
Figure 2:
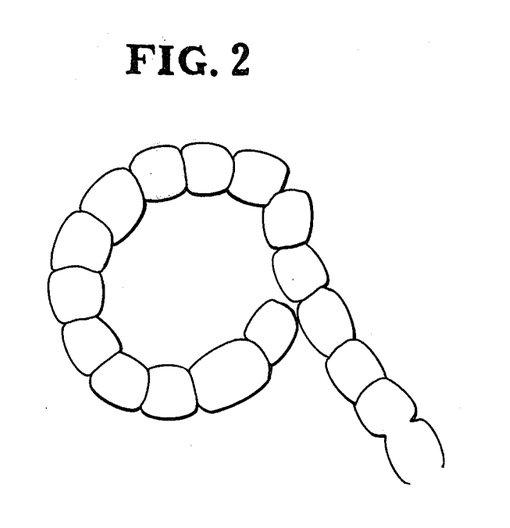

FIG. 1 is a photomicrograph (at a magnification of 800X) showing the strain as incubated at 28° C. for 14 days on glycerin-asparagine agar medium, while FIG. 2 is a electronmicrograph (at a magnification of 9000X) showing the strain as incubated at 28° C. for 14 days on oatmeal agar medium. These photographs show that spore forming mycelia of the strain are branched out in a simple fashion from a long stem formed in an aerial mycelium and have two to three turns of spiral portions at the ends of branches. A very few spore forming mycelia do not have a stem and are in the form of irregular complex branches.

An observation under a scanning electron microscope reveals that spores are smooth-surfaced, are cylindrical to ellipsoidal in shape and are about 0.7 to 1.0×0.9 to 1.6μ in size. Usually about 15 to 40 spores are connected together in the form of a chain.

II. Cultural characteristics (1) Yeast-malt agar medium
  (a) Abundant growth. Markedly wrinkled.
  (b) Aerial mycelia are moderate, powdery and covert tan (2 ge) to white.
  (c) Substrate mycelia are light wheat (2 ea) on the reverse side.
  (d) Soluble pigment is honey gold (2 ic).
(2) Oatmeal agar medium (a) Moderate growth.
(b) Aerial mycelia are abundant, powdery and beige (3 ge). Many black hygroscopic patches develop later and spread entirely.
(c) Substrate mycelia are light beige (3 ec) on the reverse side.
(d) Soluble pigment is honey gold (2 ie).

(3) Inorganic salts-starch agar medium
(a) Abundant growth.
(b) Aerial mycelia are abundant, powdery and covert gray (2 fe). Many black hygroscopic patches develop later and spread entirely.
(c) Substrate mycelia are dull gold (2 ng) on the reverse side.
(d) Soluble pigment is light citron gray (1 ec).

(4) Glycerin-asparagine agar medium
(a) Abundant growth.
(b) Aerial mycelia are abundant, powdery and beige (3 ge). Many black hygroscopic patches develop later and spread entirely.
(c) Substrate mycelia are gold (1½ lc) on the reverse side.
(d) Soluble pigment is pale yellow (1 ca).

(5) Peptone-yeast-iron agar medium
(a) Moderate growth. Slightly wrinkled.
(b) Aerial mycelia, none.
(c) Substrate mycelia are cream (1½ ca) on the reverse side.
(d) Production of soluble pigment, none.

(6) Tyrosine agar medium
(a) Abundant growth. Slightly wrinkled.
(b) Aerial mycelia are abundant, powdery and covert gray (2 fe). Black hygroscopic patches develop later and spread entirely.
(c) Substrate mycelia are gold (1½ pc) on the reverse side.
(d) Soluble pigment is honey gold (2 ic).

(7) Sucrose-nitrate agar medium
(a) Abundant growth, flat.
(b) Aerial mycelia, none.
(c) Substrate mycelia are citron yellow (1 lc) on the reverse side.
(d) Soluble pigment is canary yellow (1 ea).

(8) Glucose-asparagine agar medium
(a) Moderate growth.
(b) Aerial mycelia are abundant, powdery and covert gray (2 fe). Blackish brown and greenish patches develop from the periphery later and spread entirely.
(c) Substrate mycelia are gold (1½ lc) on the reverse side.
(d) Soluble pigment is cream (1½ ca).

(9) Nutrient agar medium
(a) Moderate growth.
(b) Aerial mycelia, none.
(c) Substrate mycelia are yellow tint (1 ba) on the reverse side.
(d) Production of soluble pigment, none.

(10) Calcium maleate agar medium
(a) Moderate growth, flat.
(b) Aerial mycelia, none.
(c) Substrate mycelia are canary yellow (1 ea) on the reverse side.
(d) Production of soluble pigment, none.

(11) Bennet's agar
(a) Abundant growth. Wrinkled.
(b) Aerial mycelia are abundant, powdery and silver gray (3 fe). Black hygroscopic patches develop later and spread entirely.
(c) Substrate mycelia are mustard (2 le) on the reverse side.
(d) Soluble pigment is light antique gold (1½ ic).

The strain was incubated on the above media all at 28° C. for 21 days. The color are indicated according to Color Harmony Manual (Container Corporation of America).

III. Physiological properties (1) Optimum temperature for growth: 28°–30° C. (No growth below 10° C. and above 45° C.)
(2) Optimum pH for growth: 6.5–8.5 (No growth below pH 4.0 and above pH 11.0.)
(3) Liquefaction of gelatin: Negative
(4) Hydrolysis of starch: Positive
(5) Coagulation of skim milk: Negative
(6) Peptonization of skim milk: Positive (acidic)
(7) Reduction of nitrate: Negative
(8) Production of melanoid pigment: Negative
(9) NaCl tolerance:
   Growth at 7%
   No growth at 10%
(10) Utilization of carbon sources:

| | |
|---|---|
| D-Glucose | ++ |
| L-Arabinose | ++ |
| Sucrose | ++ |
| D-Xylose | ++ |
| Inositol | ++ |
| D-Mannitol | ++ |
| D-Fructose | ++ |
| Rhamnose | ++ |
| Raffinose | ++ |
| Cellulose | − |

(The mark "++" means "well utilized" and "−" means "not utilized.")

IV. Type of cell wall

The type of the cell wall according to the classification of Lechevalier et al. is I type (LL-diaminopimelic acid).

Based on the above mycological characteristics, the strain was taxonomically investigated with the following results.

With reference to H. D. Tresner and E. J. Backus, Applied Microbiology, 4, 243–250 (1956), the strain has the three fundamental characteristics of *Streptomyces hygroscopicus* that spore forming mycelia extend as short side branches from the long stem of an aerial mycelium and have at least two turns of spiral portions at the ends of the branches, that the mature aerial mycelia are brownish gray and that they exhibit distinctly black hygroscopic properties. Investigations with reference to the following pieces of literature also show that the present strain belongs to *Streptomyces hygroscopicus*.

Bergey's Manual of Determinative Bacteriology, 8th Edition (1974).

Waksman, The Actinomycetes, Vol. 2 (1961).

International Journal of Systematic Bacteriology, Vol. 18, pp. 69–189 (1968), Vol. 18, pp. 279–392 (1968), Vol. 19, pp. 391–512 (1969) and Vol. 22, pp. 265–394 (1972).

The results listed in Table 4 below were obtained from the comparison of the present strain with a typical strain, *Streptomyces hygroscopicus* (Jensen), Waksman and Henrici (1948), and with an ISP standard strain, *Streptomyces hygroscopicus* ISP 5578.

TABLE 4

| Characteristics | Present strain | Hygroscopicus (Jensen) | ISP standard strain |
|---|---|---|---|
| Spore chain morphology | Spiral | Spiral | Spiral |
| Spore surface | Smooth | Smooth | Warty |
| Aerial mass color | Gray | Gray | Gray |
| Production of melanoid pigment | None | None | None |
| Production of soluble pigment | Pale yellow to yellow | Yellow | None or trace of yellow |
| Liquefaction of gelatin | − | + | |
| Hydrolysis of starch | + | + | |
| Coagulation of skim milk | − | − | |
| Peptonization of skim milk | + | + | |
| Reduction of nitrate | − | − | |
| NaCl tolerance | 7%–10% | | 7%–10% |
| Utilization of carbon sources | | | |
| D-Glucose | + | | + |
| L-Arabinose | + | | + |
| Sucrose | + | | − |
| D-Xylose | + | | + |
| i-Inositol | + | | + |
| D-Mannitol | + | | + |
| D-Fructose | + | | + |
| Rhamnose | + | | + |
| Raffinose | + | | − |

The plus sign stands for "positive" or "utilized," and the minus sign for "negative" or "not utilized," the same as in Table 5 to follow.

The above table indicates that the present strain is distinct from *Streptomyces hygroscopicus* (Jensen) in respect of the liquefaction of gelatin. The present strain also differs from the Jensen strain in that the former involves no development of aerial mycelia on sucrose-nitrate agar medium and on nutrient agar medium, whereas the latter involves development of aerial mycelia on such media.

Furthermore the present strain apparently differs from the ISP standard strain in the spore surface as well as in the utilization of carbon sources.

Since the present strain differs from the above-mentioned known strains of *S. hygroscopicus*, the present strain was further compared with four subspecies of *S. hygroscopicus* described in Bergey's Manual (8th ed.), with the results given in Table 5 below. The physiological characteristics of these species are based on the following literature.

Subspecies 1: *Streptomyces hygroscopicus* subsp. *angustmyceticus*

The Journal of Antibiotics, Ser. A, Vol. 7, pp. 116–119 (1954).

Subspecies 2: *Streptomyces hygroscopicus* subsp. *decoyicus*

Antibiotics and Chemotherapy, Vol. 9, pp. 427–431 (1957).

Subspecies 3: *Streptomyces hygroscopicus* subsp. *glebosus*

The Journal of Antibiotics, Ser. A, Vol. 15, pp. 21–27 (1962).

Subspecies 4: *Streptomyces hygroscopicus* subsp. *ossamyceticus*

The Journal of Antibiotics, Ser. A, Vol. 18, pp. 82–88 (1965).

TABLE 5

| Characteristics | Present strain | Subspecies 1 | Subspecies 2 | Subspecies 3 | Subspecies 4 |
|---|---|---|---|---|---|
| Spore chain morphology | Spiral | Spiral | Spiral | Spiral | Spiral |
| Spore surface | Smooth | Smooth | Smooth | Smooth | Smooth |
| Aerial mass color | Gray | Gray | Gray | Gray | Gray |
| Production of melanoid pigment | − | − | − | − | + |
| Production of soluble pigment | Pale yellow to yellow | None | Pale yellow to yellow | None | None or yellowish brown |
| Liquefaction of gelatin | − | + | + | − | − |
| Hydrolysis of starch | + | + | + | + | + |
| Coagulation of skim milk | − | − | − | − | − |
| Peptonization of skim milk | + | + | − | − | − |
| Reduction of nitrate | − | − | − | + | + |
| NaCl tolerance | 7%–10% | 10%–13% | 10%–13% | | |
| Utilization of carbon sources | | | | | |
| D-Glucose | + | + | + | + | + |
| L-Arabinose | + | − | − | − | + |
| Sucrose | + | + | − | + | + |
| D-Xylose | + | − | + | − | + |
| i-Inositol | + | − | + | + | + |
| D-Mannitol | + | + | + | + | + |
| D-Fructose | + | + | + | + | + |
| Rhamnose | + | − | − | − | + |
| Raffinose | + | ± | − | + | + |

Table 5 shows that the present strain is in agreement with the subspecies 4 in utilization of carbon sources but is distinct therefrom in the production of melanoid pigment, peptonization of skim milk and reduction of nitrate and differs from the subspecies 1 to 3 in the utilization of carbon sources.

The characteristics described above indicate that the present strain, although belonging to *Streptomices hygroscopicus*, is distinct from the type strain, ISP standard strain, and the strains belonging to subspecies. Furthermore the antibiotic according to this invention has never been isolated from the strains of any known species or subspecies. Thus we have found the present strain to be novel and named the strain *Streptomyces hygroscopicus* subsp. *hiwasaensis* FB-5. An application for the deposition of the microorganism was filed with Fermentation Research Institute of Agency of Industrial Science and Technology, Japan as Application No. 4573, and the strain has been deposited in the Institute as FERM-P No. 4573. The strain has been deposited also in American Type Culture Collection (ATCC) as ATCC No. 31613 since Mar. 6, 1980.

International Journal of Systematic Bacteriology, Vol. 18, p. 154 (1968) and Waksman, The Actinomycetes, Vol. 2, p. 254 (1961) state the characteristics of *Streptomyces orientalis* which affords vancomycin that appears most analogous to the antibiotic of the invention, OA-7653 substance. The aerial mycelium is not spiral, is whitish on yeast-malt agar and glycerin-asparagine agar media and whitish to grayish on inorganic salts starch agar media and involves poor development on oatmeal agar medium. The characteristics are therefore entirely different from those of the microorganism utilized in the present invention.

The antibiotic of this invention, OA-7653 substance, can be obtained by incubating *Streptomyces hygroscopicus* subsp. *hiwasaensis* FB-5 on a culture medium and isolating the substance from the resulting culture.

The strain is incubated with use of a usual liquid or solid culture medium. It is preferable to use a liquid medium for shake culture or for submerged culture with aeration and agitation.

The fermentation medium may have a composition generally used for the culture of common actinomycetes. Examples of useful carbon sources are starch, glucose, glycerin, etc. Examples of useful nitrogen sources are soybean flour, peptone, meat extract, cotton seed flour, inorganic salts such as ammonium sulfate and sodium nitrate, etc. When desired, the medium my further incorporate sodium chloride, calcium carbonate, phosphate, magnesium sulfate and like inorganic salts.

Preferably the strain is incubated at a medium pH of 6.5 to 7.5 and at a temperature of 28° to 30° C. With use of a liquid medium, the accumulated yield of the present substance reaches an approximate maximum about 72 hours after the start of incubation.

The present substance produced and accumulated in the culture can be collected by usual methods utilizing the physicochemical properties of the substance, for example, by resorting to the difference in adsorption force of ion exchange resin, silica gel, Sephadex (product of Sei Kagaku Kogyo Co., Ltd., Japan), active carbon, etc., or to the difference in partition ratio between two liquids. Such methods are usable in combination. Stated more specifically the culture is filtered or centrifuged for the removal of the cells, the resulting supernatant is subjected to active carbon column chromatography, Dowex 50W×4 column chromatography, Ecteaolacellulose column chromatography, Dowex 50W column chromatography and silica gel column chromatography in the order mentioned for elution, and the active fractions are collected and distilled for the removal of solvent, whereby OA-7653 substance, the antibiotic of the invention, can be isolated for recovery.

For use as antibacterial compositions, the substance of the invention is formulated into pharmaceutical preparations in combination with usual carriers. Examples of useful carriers are those usually used for preparing medicinal compositions in the desired form, such as diluents and excipients including filler, extender, binder, wetting agent, disintegrator, surfactant and glazing agent.

The antibacterial compositions can be in any of various dosage forms in accordance with the contemplated purpose of treatment. Typically they are in the form of tablets, pills, powders, solutions, suspensions, emulsions, granules, capsules, suppositories, injections (solutions, suspensions, etc.), ointments, etc. For the preparation of tablets, extensive use may be made of carriers already known in the art. Useful examples are excipients such as lactose, white sugar, sodium chloride, glucose solution, urea, starch, calcium carbonate, kaolin, crystalline cellulose and silicic acid; binders such as water, ethanol, propanol, syrup, glucose, starch solution, gelatin solution, carboxymethylcellulose, shellac, methylcellulose, potassium phosphate and polyvinylpyrrolidone; disintegrators such as dried starch, sodium alginate, agar powder, laminaria powder, sodium hydrogencarbonate, calcium carbonate, Tween, sodium lauryl sulfate, glyceryl monostearate, starch and lactose; disintegration suppressants such as white sugar, stearin, cacao butter and hydrogenated oils; absorption promoters such as quaternary ammonium salt and sodium lauryl sulfate; humectants such as glycerin and starch; adsorbents such as starch, lactose, kaolin, bentonite and colloidal silicic acid; glazing agents such as purified talc, stearic acid salts, boric acid powder and polyethylene glycol; etc. For the preparation of pills, a wide variety of carriers are usable which are already known in the art, useful examples being excipients such as glucose, lactose, starch, cacao fat, hardened vegetable oils, kaolin and talc; binders such as gum arabic powder, tragacanth powder, gelatin and ethanol; disintegrators such as laminaria and agar; etc. When desired, tablets can be provided with a usual coating. Thus useful are sugar-coated, gelatin-coated, enteric coated, film-coated, double-layer and multiple-layer tablets. Suppositories may be formulated with use of a wide variety of known carriers, such as polyethylene glycol, cacao fat, higher alcohols, esters of higher alcohols, gelatin, and semi-synthetic glycerides. The solutions and suspensions for injection should be sterilized and are preferably isotonic with the blood. For the preparation of such solutions, emulsions and suspensions, any diluent is usable which is usually used in the art. Examples of useful diluents are water, ethyl alcohol, propylene glycol, ethoxylated isostearyl alcohol, polyoxyisostearyl alcohol, polyoxyethylene sorbitol, sorbitan esters and the like. For the preparation of antibacterial solutions, sodium chloride, glucose or glycerin may be incorporated therein in an amount sufficient to render the solutions isotonic. Such solutions may further incorporate usual solubilizing agents, buffers, analgesics, preservatives, etc. The antibacterial compositions may contain coloring agents, preservatives, perfumes, flavoring agents, sweetening agents, etc. as well as other drugs. For the preparation of pastes, creams and gels, a wide variety of diluents are usable which are known in the art, useful examples being white petrolatum, paraffin, glycerin, cellulose derivatives, polyethylene glycol, silicone, bentonite, etc.

The amount of the substance of this invention to be contained in the antibacterial compositions is not specifically limited but can be suitably determined over a wide range. Usually the amount is about 1 to about 70% by weight of the whole composition.

The antibacterial compositions are not specifically limited in the mode of administration but can be given by a suitable method in accordance with the particular form of the composition. For example, tablets, pills, solutions, suspensions, emulsions, granules and capsules are administered orally. Injections are given intravenously, singly or as admixed with an auxiliary solution of glucose, amino acids, etc. When desired, injections are singly given intramuscularly, intradermally, subcutaneously or intraperitoneally. Suppositories are given to the rectum, while ointments are applied by coating.

The antibacterial compositions are given at a dose suitably determined according to the purpose, symptoms, etc. Usually the compositions are administered in an amount of about 100 mg to about 2 g/body/day, calculated as the present substance, in three to four divided doses.

The substance or antibacterial compositions of this invention are usable as uniformly admixed with feed for animals. The amount of the active component to be used is about 10 to about 100 g per ton of the feed although suitably variable with the kind of the animal and the degree and kind of infection. When fed to animals as admixed with the feed, the present substance is useful for the prevention or treatment of infections caused by various bacteria.

The invention will be described below in greater detail with reference to the following example and preparation examples.

EXAMPLE 1

*Streptomyces hygroscopicus* subsp. *hiwasaensis* FB-5 is inoculated in a liquid medium having a pH of 7 and composed of 1% of starch, 0.5% of glucose, 0.5% of glycerin, 0.5% of soybean flour, 0.3% of meat extract (Wako Meat Extract, prepared from fin whale meat and bonito meat by Wako Co., Ltd., Japan), 0.3% of Polypeptone (product of Daigo Eiyo Kagaku Co., Ltd., Japan), 0.5% of sodium chloride, 0.3% of calcium carbonate and distilled water. The strain is incubated at 28° C. for 48 hours.

A culture medium (20 liters) having the same composition as above and placed in a 30-liter stainless steel container is inoculated with the inoculum in an amount of 1% based on the medium, and the inoculum is incubated at 28° C. for 72 hours with aeration and agitation. The medium is aerated at a rate of 20 liters per minute, with the agitating blade driven at 300 r.p.m.

The resulting culture is centrifuged for the removal of cells. The supernatant (18 liters) is applied to an active carbon column for adsorption, washed with water and thereafter eluted with 1.5 liters of a mixture of 2 N aqueous solution of ammonia and methanol (1:1 by volume). The resulting solution is distilled in a vacuum for the removal of ammonia and methanol. The residue is adjusted to a pH of 3 with 2 N aqueous solution of dihydrochloric acid and then applied to a Dowex 50W×4 (Na+ type) column for adsorption. After washing the column with water, gradient elution is conducted with 1 liter of 0.1 mole phosphoric acid buffer (pH 7.0) and 1 mole of NaCl in 1 liter of 0.1 mole carbonate buffer (pH 10.0). The resulting active fractions are collected, and the combined solution is diluted with the same quantity of distilled water, adjusted to a pH of 3 with 2 N aqueous solution of hydrochloric acid and then applied to a Dowex 50W×4 (NH4+ type) for adsorption. After washing the column with water, the active substance is eluted with 500 ml of 0.1 N aqueous ammonia solution. The resulting active fractions are collected, and the ammonia is removed therefrom in a vacuum. The residue is adjusted to a pH of 8.0 with 1 N aqueous solution of sodium hydroxide and then applied to an Ecteaolacellulose (Cl− type, product of Whatman) column for adsorption. After washing the column with water, gradient elution is conducted with 1 liter of distilled water and 1 liter of 1 mole aqueous sodium chloride solution. The resulting active fractions are collected, and the combined solution is adjusted to a pH of 3 with 0.2 N aqueous solution of hydrochloric acid and then applied to a Dowex 50W×4 (NH4+ type) column for adsorption. After washing the column with water, the active substance is eluted with 500 ml of 0.1 N aqueous ammonia solution. The resulting active fractions are collected and concentrated in a vacuum. With addition of 3.0 g of silica gel (Wako Gel C200, product of Wako Co., Ltd., Japan), the concentrate is further concentrated to dryness. The product is suspended in 20 ml of 90% aqueous ethanol solution, and the suspension is applied to a column of silica gel (Wako Gel C200). After washing the column with 100 ml of 90% aqueous ethanol solution, the active substance is eluted with 500 ml of 70% aqueous ethanol solution. The resulting active fractions are collected, concentrated in a vacuum and then freeze-dried, giving 1 g of OA-7653 substance of the invention in the form of white particulate crystals. The product has the physicochemical properties already described.

| Preparation Example 1 | |
| --- | --- |
| Substance of the invention | 200 mg |
| Glucose | 250 mg |
| Distilled water for injection | Suitable amount |
| Total amount | 5 ml |

The solution of above composition is placed into a 5-ml ampule. With the air in the ampule replaced by nitrogen, the solution is sterilized at 121° C. for 15 minutes to obtain an injection solution.

| Preparation Example 2 | |
| --- | --- |
| Substance of the invention | 100 g |
| Avicel (trade mark of Asahi Chemical Industry Co., Ltd., JAPAN) | 40 g |
| Corn starch | 30 g |
| Magnesium stearate | 2 g |
| TC-5 (trade mark of Shin-etsu Kagaku Kogyo Co., Ltd., Japan for hydroxypropyl-methyl cellulose) | 10 g |
| Polyethylene glycol-6000 | 3 g |
| Castor oil | 40 g |
| Methanol | 40 g |

The substance of the invention, Avicel, corn starch and magnesium stearate are mixed together, ground and made into tablets with use of the plungers and mortars of ϕ10 mm. The tablets are coated with a film coating composition comprising TC-5, polyethylene glycol-6000, castor oil and methanol to obtain coated tablets of the above composition.

| Preparation Example 3 | |
| --- | --- |
| Substance of the invention | 2 g |
| Purified hydrous lanolin | 5 g |
| White beeswax | 5 g |

| Preparation Example 3 | |
|---|---|
| White petrolatum | 88 g |
| Total amount | 100 g |

White beeswax is heated to a liquid state, and the compound of the invention, purified lanolin and white petrolatum are added thereto. The mixture is heated to a liquid state and thereafter stirred until the mixture starts to solidify to obtain an ointment of the above composition.

What we claim is:

1. OA-7653 substance comprising L-glutamic acid and glucose as components and having the following characteristics:
   a. sparingly soluble in 0.1 N aqueous solution of hydrochloric acid, insoluble in methanol, ethanol, butanol, acetone and ethyl acetate and soluble in 0.1 N aqueous solution of sodium hydroxide,
   b. positive when subjected to iodine reaction, ninhydrin reaction, Molisch reaction and Ehrlich's reaction,
   c. a specific rotatory power of $[\alpha]_D^{23.5} = +76.5°$ (C=0.463, water),
   d. a composition comprising 46.10% carbon, 4.47% hydrogen and 7.18% nitrogen, as determined by elementary analysis,
   e. a molecular weight of about 2000, as determined by ultra-centrifugal analysis,
   f. an isoelectric point at a pH of 5–6, as determined by electrophoresis,
   g. an IR absorption spectrum in KBr disk with significant absorption maxima at the following frequencies (cm$^{-1}$): 3280 (s), 1660 (s), 1640 (s), 1515 (s), 1490 (s), 1395 (s), 1235 (s), 1150 (m), 1062 (s) and 1020 (s),
   h. UV absorption spectra with absorption maxima at 278 mµ in 0.1 N aqueous hydrochloric acid solution, at 278 mµ in distilled water and at 298 mµ in 0.1 N aqueous sodium hydroxide solution,
   i. a $^1$H-NMR spectrum in dimethyl sulfoxide substituted with deuterium with the following peaks:

| No. | ppm | No. | ppm | No. | ppm |
|---|---|---|---|---|---|
| 1 | 1.05–1.35 | 5 | 3.0–4.1 | 9 | 6.6–7.0 |
| 2 | 1.60–2.0 | 6 | 4.2–4.9 | 10 | 7.0–7.55 |
| 3 | 2.2 | 7 | 5.05–5.6 | 11 | 7.6–8.0 |
| 4 | 2.50 | 8 | 6.3–6.5 | | | j. a $^{13}$C-NMR spectrum in dimethyl sulfoxide substituted with deuterium with the following peaks:

| No. | ppm | No. | ppm | No. | ppm |
|---|---|---|---|---|---|
| 1 | 173.2 | 14 | 148.7 | 27 | 105.9 |
| 2 | 173.0 | 15 | 146.8 | 28 | 104.6 |
| 3 | 172.4 | 16 | 138.3 | 29 | 102.3 |
| 4 | 172.2 | 17 | 136.5 | 30 | 96.3 |
| 5 | 170.8 | 18 | 135.5 | 31 | 73.6 |
| 6 | 169.7 | 19 | 134.1 | 32 | 69.3 |
| 7 | 169.0 | 20 | 131.6 | 33 | 62.5 |
| 8 | 167.1 | 21 | 129.7 | 34 | 60.6 |
| 9 | 157.0 | 22 | 128.8 | 35 | 56.7 |
| 10 | 156.8 | 23 | 127.8 | 36 | 53.9 |
| 11 | 155.8 | 24 | 125.3 | 37 | 31.1 |
| 12 | 149.7 | 25 | 121.5 | 38 | 9.6 |
| 13 | 149.5 | 26 | 117.9 | | | k. Rf values, as determined by silica gel thin-layer chromatography, of zero with use of butanol-acetic acid-water (4:1:1 by volume) as a developing solvent, of zero with use of propanol-2 N aqueous ammonia solution (7:3 by volume) as a developing solvent, of 0.45 with use of chloroform-ethanol-water (4:7:2 by volume) as a developing solvent, and of 0.8 with use of ethanol-water (7:3 by volume) as a developing solvent, and
   l. Rf values, as determined by paper chromatography, of 0.83 with use of butanol-acetic acid-water (4:3:7 by volume) as a developing solvent, and of 0.76 with use of butanol-pyridine-water (4:3:7 by volume) as a developing solvent.

2. An antibacterial composition comprising as an active ingredient an antibacterially effective amount of the OA-7653 substance of claim 1 and a pharmaceutically acceptable carrier.

* * * * *